(12) United States Patent
MacLaughlan et al.

(10) Patent No.: US 6,608,047 B2
(45) Date of Patent: Aug. 19, 2003

(54) USE OF LOW DOSAGE AMOUNT OF SPIRONOLACTONE FOR TREATMENT OF CARDIOVASCULAR DISEASE

(75) Inventors: Todd E. MacLaughlan, Grayslake, IL (US); Alfonso T. Perez, Lake Forest, IL (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 10/054,799

(22) Filed: Jan. 22, 2002

(65) Prior Publication Data

US 2003/0087884 A1 May 8, 2003

Related U.S. Application Data

(63) Continuation of application No. 09/756,892, filed on Jan. 9, 2001, now Pat. No. 6,391,867, which is a continuation of application No. 09/458,532, filed on Dec. 9, 1999, now abandoned, which is a continuation of application No. 09/293,506, filed on Apr. 15, 1999, now abandoned, which is a continuation of application No. 09/093,130, filed on Jun. 8, 1998, now abandoned, which is a continuation of application No. 08/875,534, filed as application No. PCT/US96/01769 on Feb. 9, 1996, which is a continuation of application No. 08/386,793, filed on Feb. 10, 1995, now abandoned.

(51) Int. Cl.$^7$ .............................................. A61K 31/585
(52) U.S. Cl. ........................................................ 514/175
(58) Field of Search ......................................... 514/175

(56) References Cited

U.S. PATENT DOCUMENTS 5,668,125 A * 9/1997 Weber ........................ 514/175
6,391,867 B2 * 5/2002 MacLaughlan et al. ..... 514/175

* cited by examiner

*Primary Examiner*—Raymond Henley, III
(74) *Attorney, Agent, or Firm*—Joseph R. Scuh; J. Timothy Keane

(57) ABSTRACT

Use of low dosages of an aldosterone receptor antagonist, spironolactone, is described for treatment of circulatory disorders. This therapy would be particularly useful to treat or retard the development of congestive heart failure, while avoiding or reducing aldosterone-antagonist-induced side effects, such as hyperkalemia.

5 Claims, 5 Drawing Sheets

USE OF LOW DOSAGE AMOUNT OF SPIRONOLACTONE FOR TREATMENT OF CARDIOVASCULAR DISEASE

This is a continuation of application Ser. No. 09/756,892, filed on Jan. 9, 2001, now U.S Pat. No. 6,391,867, wish is a continuation of application Ser. No. 09/458,532, filed on Dec. 9, 1999, now abandoned, which is a continuation of prior application Ser. No. 09/293,506 filed on Apr. 15, 1999, now abandoned, which is a continuation of application Ser. No. 09/093,130 filed on Jun. 8, 1998, now abandoned, which is a continuation of prior application Ser. No. 08/875,534 filed on Jul. 30, 1997, which is a 371 application of Ser. No. PCT/US96/01769, filed on Feb. 9, 1996, which is a continuation of application Ser. No. 08/386,793, filed on Feb. 10, 1995, now abandoned.

FIELD OF THE INVENTION

Spironolactone, an aldosterone receptor antagonist, is described for use in treatment of circulatory disorders, including cardiovascular diseases such as heart failure, hypertension and congestive heart failure. Of particular interest is a therapy using spirolactone at a low dosage at which side-effects are reduced or avoided.

BACKGROUND OF THE INVENTION

Myocardial (or cardiac) failure, that is, heart failure ("HF"), whether a consequence of previous myocardial infarction(s), heart disease associated with hypertension, or primary cardiomyopathy, is a major health problem of worldwide proportions. The incidence of symptomatic heart failure has risen steadily over the past several decades.

In clinical terms, decompensated cardiac failure consists of a constellation of signs and symptoms that arise from congested organs and hypoperfused tissues to form congestive heart failure (CHF) syndrome. Congestion is caused largely by increased venous pressure and by inadequate sodium ($Na^+$) excretion, relative to dietary $Na^+$ intake, and is importantly related to circulating levels of aldosterone (ALDO). An abnormal retention of $Na^+$ occurs via tubular epithelial cells throughout the nephron, including the later portion of the distal tubule and cortical collecting ducts, where ALDO receptor sites are present.

ALDO is the body's most potent mineralocorticoid hormone. As connoted by the term mineralocorticoid, this steroid hormone has mineral-regulating activity. It promotes Na+ reabsorption not only in the kidney, but also from the lower gastrointestinal tract and salivary and sweat glands, each of which represents classic ALDO-responsive tissues. ALDO regulates Na+ and water resorption at the expense of potassium ($K^+$) and magnesium ($Mg^{2+}$) excretion.

ALDO can also provoke responses in non-epithelial cells. Elicited by a chronic elevation in plasma ALDO level that is inappropriate relative to dietary $Na^+$ intake, these responses can have adverse consequences on the structure of the cardiovascular system. Hence, ALDO can contribute to the progressive nature of myocardial failure for multiple reasons.

Multiple factors regulate ALDO synthesis and metabolism, many of which are operative in the patient with myocardial failure. These include renin as well as non-renin-dependent factors (such as $K^+$, ACTH) that promote ALDO synthesis. Hepatic blood flow, by regulating the clearance of circulating ALDO, helps determine ALDO plasma concentration, an important factor in heart failure characterized by reduction in cardiac output and hepatic blood flow.

The renin-angiotensin-aldosterone system ("RAAS") is one of the hormonal mechanisms involved in regulating pressure/volume homeostasis and also in the development of hypertension, a precursor condition implicated in the progression of more serious cardiovascular diseases such as congestive heart failure. Activation of the renin-angiotensin-aldosterone system begins with secretion of the enzyme renin from the juxtaglomerular cells in the kidney. The enzyme renin acts on a naturally-occurring substrate, angiotensinogen, to release a decapeptide, Angiotensin I. This decapeptide is cleaved by angiotensin converting enzyme ("ACE") to provide an octapeptide, Angiotensin II, the primary active species of this system. This octapeptide, angiotensin II, is a potent vasoconstrictor and also produces other physiological effects such as stimulating aldosterone secretion, promoting sodium and fluid retention, inhibiting renin secretion, increasing sympathetic nervous system activity, stimulating vasopressin secretion, causing positive cardiac inotropic effect and modulating other hormonal systems.

Emphasis has been placed on minimizing hyperaldosteronism as a basis for optimizing patient treatment. This includes the importance of ALDO-receptor antagonism both in patients treated with conventional diuretic programs and in patients treated with angiotensin-converting enzyme (ACE) inhibitors, who are often constrained to small doses of ACE inhibitor because of orthostatic hypotension. Such patients may demonstrate a recurrence of heart failure symptoms likely related to elevations in plasma ALDO levels.

Many aldosterone receptor blocking drugs and their effects in humans are known. For example, spironolactone is a drug which acts at the mineralocorticoid receptor level by competitively inhibiting aldosterone binding. This steroidal compound has been used for blocking aldosterone-dependent sodium transport in the distal tubule of the kidney in order to reduce edema and to treat essential hypertension and primary hyperaldosteronism [F. Mantero et al, *Clin. Sci. Mol. Med.*, 45 (Suppl 1), 219s–224s (1973)]. Spironolactone is also used commonly in the treatment of other hyperaldosterone-related diseases such as liver cirrhosis and congestive heart failure [F. J. Saunders et al, *Aldactone; Spironolactone: A Comprehensive Review*, Searle, N.Y. (1978)]. Progressively-increasing doses of spironolactone from 1 mg to 400 mg per day [i.e., 1 mg/day, 5 mg/day, 20 mg/day] was administered to a spironolactone-intolerant patient to treat cirrhosis-related ascites [P. A. Greenberger et al, *N. Eng. Reg. Allercy Proc.*, 7(4), 343–345 (July–August, 1986)]. It has been recognized that development of myocardial fibrosis is sensitive to circulating levels of both Angiotensin II and aldosterone, and that the aldosterone antagonist spironolactone prevents myocardial fibrosis in animal models, thereby linking aldosterone to excessive collagen deposition [D. Klug et al, *Am. J. Cardiol.*, 71(3), 46A–54A (1993)]. Spironolactone has been shown to prevent fibrosis in animal models irrespective of the development of left ventricular hypertrophy and the presence of hypertension [C.G. Brilla et al, *J. Mol. Cell. Cardiol.*, 25(5), 563–575 (1993)]. Spironolactone at a dosage ranging from 25 mg to 100 mg daily is used to treat diuretic-induced hypokalemia, when orally-administered potassium supplements or other potassium-sparing regimens are considered inappropriate [Physicians' Desk Reference, 46th Edn., p. 2153, Medical Economics Company Inc., Montvale, N.J. (1992)].

Previous studies have shown that inhibiting ACE inhibits the renin-angiotensin system by substantially complete blockade of the formation of Angiotensin II. Many ACE inhibitors have been used clinically to control hypertension. While ACE inhibitors may effectively control hypertension, side effects are common including chronic cough, skin rash, loss of taste sense, proteinuria and neutropenia.

Moreover, although ACE inhibitors effectively block the formation of Angiotensin II, aldostero-ne levels are not well controlled in certain patients having cardiovascular diseases. For example, despite continued ACE inhibition in hypertensive patients receiving captopril, there has been observed a gradual return of plasma aldosterone to baseline levels [J. Staessen et al, *J. Endocrinol.*, 9, 457–465 (1981)]. A similar effect has been observed for patients with myocardial infarction receiving zofenopril [C. Borghi et al, *J. Clin. Pharmacol.*, 33, 40–45 (1993)]. This phenomenon has been termed "aldosterone escape".

In a side-by-side treatment of two cohorts of rats, one cohort treated with spironolactone sub-cutaneously and the other cohort treated with captopril, spironolactone was found to prevent fibrosis in the hypertensive-rat cohort [C.G. Brilla et al, *J. Mol. Cell. Cardiol.*, 25, 563–575 (1993)].

SUMMARY OF DRAWING FIGURES

DESCRIPTION OF THE INVENTION

Figure 1:
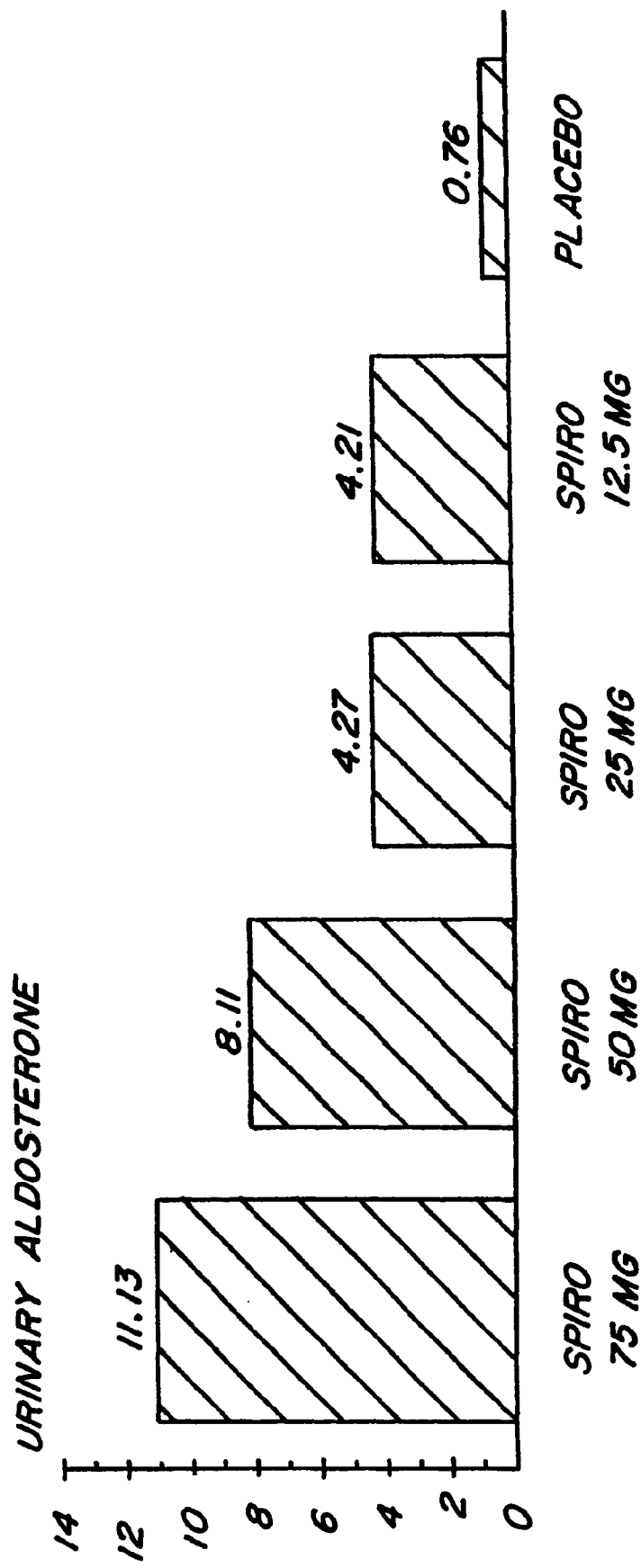
FIG. 1 shows urinary aldosterone levels at different rates of spironolactone administration (12.5 mg, 25 mg, 50 mg, 75 mg), as compared to placebo, co-administered with stable doses of ACE inhibitor and loop diuretic.

Treatment or prevention of circulatory disorders, including cardiovascular disorders such as heart failure, hypertension and congestive heart failure, is provided by a therapy comprising use of a therapeutically-effective amount of spironolactone. Preferably, spironolactone is administered in the therapy at a low dose, that is, at a dose lower than has been conventionally used in clinical situations.

The therapy of the invention would be useful, for example, to prevent or retard, in a subject, the development of congestive heart failure which typically arises from essential hypertension or from heart conditions following myocardial infarct. Such subject would not typically be suffering from an edematous condition and thus would not gain benefit from treatment with conventional diuretic therapy as with loop diuretics which can alter electrolyte balance and cause hypokalemic or hypomagnesia conditions.

The phrase "aldosterone receptor antagonist" embraces an agent or compound, or a combination of two or more of such agents or compounds, which agent or compound binds to the aldosterone receptor as a competitive inhibitor of the action of aldosterone itself at an aldosterone receptor site, such as typically found in the renal tubules, so as to modulate the receptor-mediated activity of aldosterone. Typical of such aldosterone receptor antagonists are spirolactone-type compounds. The term "spirolactone-type" is intended to characterize a steroidal structure comprising a lactone moiety attached to a steroid nucleus, typically at the steroid "D" ring, through a spiro bond configuration.

The phrase "therapeutically-effective", is intended to qualify the amount of aldosterone receptor antagonist agent for use in the therapy which will achieve the goal of improvement in cardiac sufficiency by reducing or preventing, for example, the progression of congestive heart failure, while avoiding adverse side effects typically associated with such agent.

The phrase "low-dose amount", in characterizing a therapeutically-effective amount of the aldosterone receptor antagonist agent in the combination therapy, is intended to define a quantity of such agent, or a range of quantity of such agent, that is capable of improving cardiac sufficiency while reducing or avoiding one or more aldosterone-antagonist-induced side effects, such as hyperkalemia. A dosage of spironolactone which would accomplish the therapic goal of favorably enhancing cardiac sufficiency, while reducing or avoiding side effects, would be a dosage that substantially avoids inducing diuresis, that is, a substantially non-diuresis-effective dosage.

The compound spironolactone has the following structure and formal name:

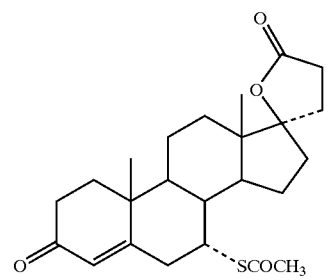

"spironolactone": 17-hydroxy-7α-mercapto-3-oxo-17α-pregn-4-ene-21-carboxylic acid γ-lactone acetate Methods to make spironolactone are described in U.S. Pat. No. 3,013,012 to Cella et al which issued Dec. 12, 1961. Spironolactone is sold by G. D. Searle & Co., Skokie, Ill., under the trademark "ALDACTONE", in tablet dosage form at doses of 25 mg, 50 mg and 100 mg per tablet.

A diuretic agent may be used in combination with spironolactone. Such diuretic agent may be selected from several known classes, such as thiazides and related sulfonamides, potassium-sparing diuretics, loop diuretics and organic mercurial diuretics.

Examples of thiazides are bendroflumethiazide, benzthiazide, chlorothiazide, cyclothiazide, hydrochlorotthiazide, hydroflumethiazode, methyclothiazide, polythiazide and trichlormethiazide.

Examples of related sulfonamides are chlorthalidone, quinethazone and metolazone.

A diuretic agent may be used in combination with spironolactone. Such diuretic agent may be selected from several known classes, such as thiazides and related sulfonamides, potassium-sparing diuretics, loop diuretics and organic mercurial diuretics.

Examples of thiazides are bendroflumethiazide, benzthiazide, chlorothiazide, cyclothiazide, hydrochlorothiazide, hydroflumethiazide, methyclothiazide, polythiazide and trichlormethiazide.

Examples of sulfonamides related to thiazides are chlorthalidone, quinethazone and metolazone.

Examples of potassium-sparing diuretics are triameterene and amiloride.

Examples of loop diuretics, i.e., diuretics acting in the ascending limb of the loop of Henle of the kidney, are furosemide and ethynacrylic acid.

Examples of organic mercurial diuretics are mercaptomerin sodium, merethoxylline procaine and mersalyl with theophylline.

Biological Evaluation

Human Clinical Trials

Spironolactone was evaluated in humans as described in the following clinical trials.

Patients: Two-hundred fourteen (214) patients with symptomatic heart failure had an ejection fraction $\leq 35\%$, a history of New York Heart Association (NYHA) functional classification III–IV six months prior to enrollment, and current classification II–IV were randomized among five treatment groups. Patients were assigned to receive either spironolactone 12.5 mg (41 patients), 25 mg (45 patients), 50 mg (47 patients), 75 mg (41 patients), or placebo (40 patients) once a day for 12 weeks. Two patients that were randomized failed to take the study medication and were excluded from the analysis. All patients were taking a stable dose of ACE inhibitor, loop diuretic, and optional digitalis for 30 days prior to the first dose of study medication. Potassium supplement therapy that was stable for 14 days prior to the first dose of study medication was also allowed. Informed consent was obtained from all patients, and the protocol was approved by each ethical committee. At enrollment all patients had normal serum potassium values (<5.5 mmol/L) and creatinine values of $\leq 2.0$ mg/dL or $\leq 180$ mmol/L. Patients were excluded from enrollment if they: (1) were diagnosed with either an acute life-threatening disease (included patients with automatic implantable cardioverter/ defibrillator), valvular disease, unstable angina, insulin-dependent diabetes, cancer (without a reoccurrence within the last five years), or primary hepatic failure; (2) were on a waiting list for a heart transplant or experienced a myocardial infarction 30 days prior to the first dose of study medication; (3) had laboratory values for hematology or biochemistry considered abnormal and clinically significant prior to the first dose of study medication; (4) received a potassium spacing diuretic within 30 days prior to the first dose of study medication.; (5) were receiving, on a regular basis, either non-steroidal anti-inflammatory drugs or aspirin >325 mg/day, steroids, dopamine agonists or antagonists, insulin or heparin; (6) were on any investigational medication within 30 days of the first dose of medication.

Study Design: This was a multinational, double-blind, randomized, parallel group study.

Laboratory Measurements: The following information was obtained from each patient at baseline:
1. Concurrent medication within the past 30 days.
2. 12-lead ECG
3. Cardiac assessments that included blood pressure, pulse, sodium retention score (general assessment of a patient's edematous state was derived from the summation of scores obtained from Table I), NYHA classification, and
4. Signs and symptoms within the past 30 days.

TABLE I

Sodium Retention Score

| Parameters | Grade | Assessment |
| --- | --- | --- |
| Rales | 0 | Absent |
|  | 1 | In lower ⅓ of lungs |
|  | 2 | In lower ⅔ of lungs |
|  | 3 | In all lung fields |
| Peripheral | 0 | Absent |
| Pitting Edema | 1 | Trace |
|  | 2 | Limited to ankles |
|  | 3 | Not limited to ankles |
|  | 4 | Anasarca |
| Weight Change | −1 | Decreased |
|  | 0 | Unchanged |
|  | 1 | Increased |
| Hepatomegaly | 0 | Absent |
|  | 1 | Present |
| S3 Gallop | 0 | Absent |
|  | 1 | Present |
| Increased Jugular | 0 | Absent |
| Venous Pressure | 1 | Present |

The following laboratory values were obtained at the pretreatment visit:

| | |
| --- | --- |
| Hematology: | White blood cell count (WBC), hematocrit, hemoglobin, platelet count. |
| Biochemistry: | Creatinine, potassium, AST, SGOT, urinary sodium/potassium ratio, bicarbonate, calcium, chloride, creatinine, creatinine clearance, magnesium, glucose, urea, uric acid. |
| Neurohormones: | Plasma renin activity, pro-atrial natriuretic factor, urinary aldosterone. |

Blood and urine samples were centrally analyzed at SciCor Laboratories. Laboratory values for urinary aldosterone and renin levels were done at the Ohio State University Laboratory in Columbus, Ohio. Pro-atrial natriuretic factor samples were evaluated at the University of Oslo Laboratory in Oslo, Norway. Patients were evaluated 9 days after beginning study medication. Documented changes in concurrent medications, signs and symptoms and drug compliance were recorded. These procedures were repeated at Week 4 and Week 8 visits. Patient information and procedures on the final visit (Week 12) was identical to the pre-treatment visit.

Statistical Analysis: Analysis of cardiac assessment changes in patient therapy and vital signs were performed for both the Intent-to-Treat (ITT) and evaluable patient groups. Analysis of demographic variables, adverse events and clinical laboratory values were performed in the ITT group. For each efficacy variable, results of each visit were examined separately. An appropriate trend test was used to test for overall dose-response. Pair-wise comparisons were made for each active dose to placebo. Significant levels for pair-wise comparisons were adjusted using the Hochberg-Bonferromi method to maintain the overall Type I error rate. All statistical methods were two-sided.

Recruitment: Two-hundred and fourteen patients were recruited from 22 study sites in eleven countries.

Patient Characteristics: Patient demographic, vital signs, and cardiac status at baseline are summarized in Table II.

TABLE II

Patient Demographics

| Demographic | Spironolactone 12.5 mg/d | Spironolactone 25 mg/d | Spironolactone 50 mg/d | Spironolactone 75 mg/d | Placebo | p-Value |
|---|---|---|---|---|---|---|
| Age (years) | 63 ± 12 | 61 ± 9 | 62 ± 13 | 62 ± 13 | 61 ± 12 | N.S. |
| Caucasian/other (%) | 93/7 | 98/2 | 93/7 | 88/12 | 97/3 | N.S. |
| Male/female (%) | 78/22 | 82/18 | 74/26 | 88/12 | 83/18 | N.S. |
| Vital Signs | | | | | | |
| Weight (kg) | 74 | 75 | 73 | 78 | 73 | N.S. |
| Blood pressure (mmHg) | | | | | | |
| Systolic | 121 | 120 | 121 | 125 | 121 | N.S. |
| Diastolic | 76 | 76 | 75 | 81 | 74 | N.S. |
| Pulse (bpm) | 76 | 74 | 76 | 74 | 71 | N.S. |
| Cardiac Status | | | | | | |
| NYHA (%) | | | | | | |
| II | 63 | 60 | 43 | 49 | 38 | |
| III | 34 | 38 | 55 | 49 | 60 | |
| IV | 2 | 2 | 2 | 2 | 2 | N.S. |
| Sodium retention score Mean value | 1.54 | 1.62 | 1.64 | 1.61 | 1.78 | N.S. |
| ACE-I (Mean dose) | | | | | | |
| Captopril (mg) | 57.3 | 57.5 | 69.7 | 59.4 | 65.4 | N.S. |
| Enalapril (mg) | 16.4 | 13.4 | 14.5 | 16.3 | 10.8 | N.S. |
| Loop Diuretic (Mean dose) | 58.8 | 82.8 | 76.9 | 84.9 | 63.2 | N.S. |
| Furosemide (mg) | | | | | | |
| Digoxin (%) | 78.0 | 77.8 | 76.6 | 80.5 | 77.5 | N.S. |
| Potassium supplement (%) | 43.9 | 37.8 | 34.0 | 39.0 | 30.0 | N.S. |

Patients ranged in age from 26 to 83 years (mean=60), 81% were male, 94% were Caucasian. At baseline 51% of the patients were NYHA Class II, 47% were Class III. With respect to sodium retention score, a statistically significant dose response was seen at Day 9 with higher doses showing more reduction in sodium retention score (p=0.019). However, this effect was not seen at later visits (p>0.20). There was an improvement in NYHA Class placebo group and in all the spironolactone groups. Although a trend toward improvement in the spironolactone group was observed, the difference was not statistically significant.

Chances in Patient Therapy: The treatment groups did not differ significantly with respect to changes in dose; of ACE inhibitor, digitalis or potassium supplements at any. visit (p≧0.11). The treatment groups did differ significantly with respect to changes in loop diuretic therapy only at Week 8 (p=0.004) in that more patients on the higher doses of spironolactone had decreases in the loop diuretic dose compared to the placebo group. This pattern was not observed at Week 12.

Chanaes in Vital Signs: Changes from baseline in vital signs at Week 12 are summarized in Table III.

At all visits the 25 mg, 50 mg, and 75 mg groups had decreases in mean systolic and diastolic blood pressure, while the placebo group had increases in mean systolic and diastolic blood pressure (both standing and supine). Dose response with respect to standing and supine diastolic blood pressure was statistically significant for all visits (p≦0.002). Dose response with respect to standing and supine blood pressure was statistically significant at Week 4, Week 8, and Week 12 (p≦0.033), but not at Day 9 (p≧0.12). No significant between-treatment differences in change from baseline in pulse were observed at any visit (p-values≧0.136). A statistically significant dose response with greater decreases in pulse in the supine position at higher doses was observed at Week 4 (p-value=0.045). Spironolactone doses of 25 and 50 mg were also significantly different from placebo (p-values≦0.043) (See FIG. 1). At Day 9 and Week 4 visits, there was a statistically significant dose response with respect to changes from baseline in body weight in that patients in the 75 mg dose group experienced more weight loss than other patients. This dose response was not observed at later visits (p≧0.062).

Clinical Laboratory Values: Table IV contains details of the different clinical laboratory values that showed statisti-

TABLE III

Mean Change in Weight and Vital Signs from Baseline to Week 12

| | Spironolactone 12.5 mg/d | Spironolactone 25 mg/d | Spironolactone 50 mg/d | Spironolactone 75 mg/d | Placebo | p-Value |
|---|---|---|---|---|---|---|
| Weight | 0.59 (3.00) | −0.16 (3.02) | 0.62 (2.05) | −0.81 (2.70) | 0.11 (2.46) | 0.109 |
| Supine systolic BP | 1.84 (11.82) | −4.46 (13.97) | −7.04 (15.83) | −5.68 (15.62) | 0.22 (13.45) | 0.036 |
| Supine diastolic BP | −0.19 (9.13) | −2.74 (9.57) | −5.11 (11.11) | −5.91 (9.05) | 1.78 (7.84) | 0.014 |
| Supine pulse (BPM) | −3.70 (9.56) | −1.40 (10.00) | −3.21 (11.27) | −1.07 (13.79) | 1.42 (9.69) | 0.422 | cally significant treatment differences with respect to mean changes at Week 12 visit compared with their respective baseline value.

TABLE IV

Week 12 Mean Change

| | Spironolactone 12.5 mg/d | Spironolactone 25 mg/d | Spironolactone 50 mg/d | Spironolactone 75 mg/d | Placebo | p-Value |
|---|---|---|---|---|---|---|
| Urinary aldosterone (nmol/D) | 4.21 | 4.27 | 8.11 | 11.13 | 0.76 | 0.002 |
| N-Terminal ANF (pmol/L) | −287.30 | −294.60 | −351.30 | −370.60 | 54.50 | 0.022 |
| PRA (NgAngl/L/s) | 9.90 | 9.33 | 13.18 | 10.23 | 0.50 | 0.002 |
| Hematocrit (%) | 0.00 | −0.02 | −0.02 | −0.03 | 0.00 | 0.002 |
| Hemoglobin (mmol/L/Fe) | 0.12 | −0.20 | −0.31 | −0.46 | 0.00 | 0.005 |
| Potassium (mmol/L) | 0.18 | 0.37 | 0.51 | 0.58 | −0.10 | 0.001 |
| Creatinine (umol/L) | 6.83 | 9.30 | 14.06 | 21.90 | −1.96 | 0.001 |
| Sodium (mmol/L) | −1.61 | −1.85 | −2.52 | −3.37 | −0.03 | 0.001 |

Figure 2:
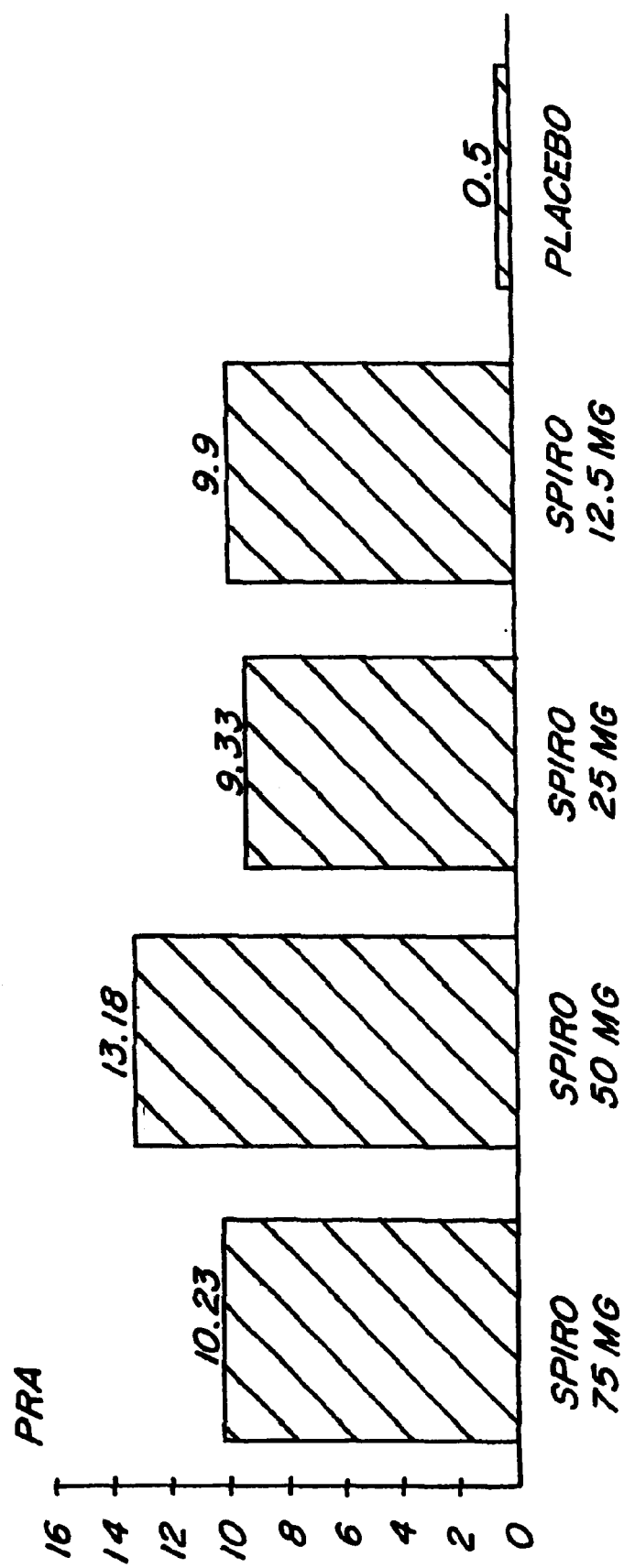
FIG. 2 shows plasma renin activity at different rates of spironolactone administration (12.5 mg, 25 mg, 50 mg, 75 mg), as compared to placebo, co-administered with stable doses of ACE inhibitor and loop diuretic.

Urinary Aldosterone (See FIG. 2): Urinary aldosterone was determined only for baseline and the 12 week visit. Urinary aldosterone excretion showed mean increases from baseline in all treatment groups ($P \leq 0.012$). Greater increases were seen at higher doses of spironolactone (p=0.002). All pair-wise comparisons between active treatment and placebo were statistically significant ($p \leq 0.009$).

Plasma Renin Activity (PRA) (See FIG. 2): A statistically significant dose-response with respect to change from baseline in PRA was seen at Day 9, Week 4 and Week 12 ($P \leq 0.001$) with higher doses of spironolactone associated with greater increases in PRA. PRA was not measured at Week 8.

Figure 3:
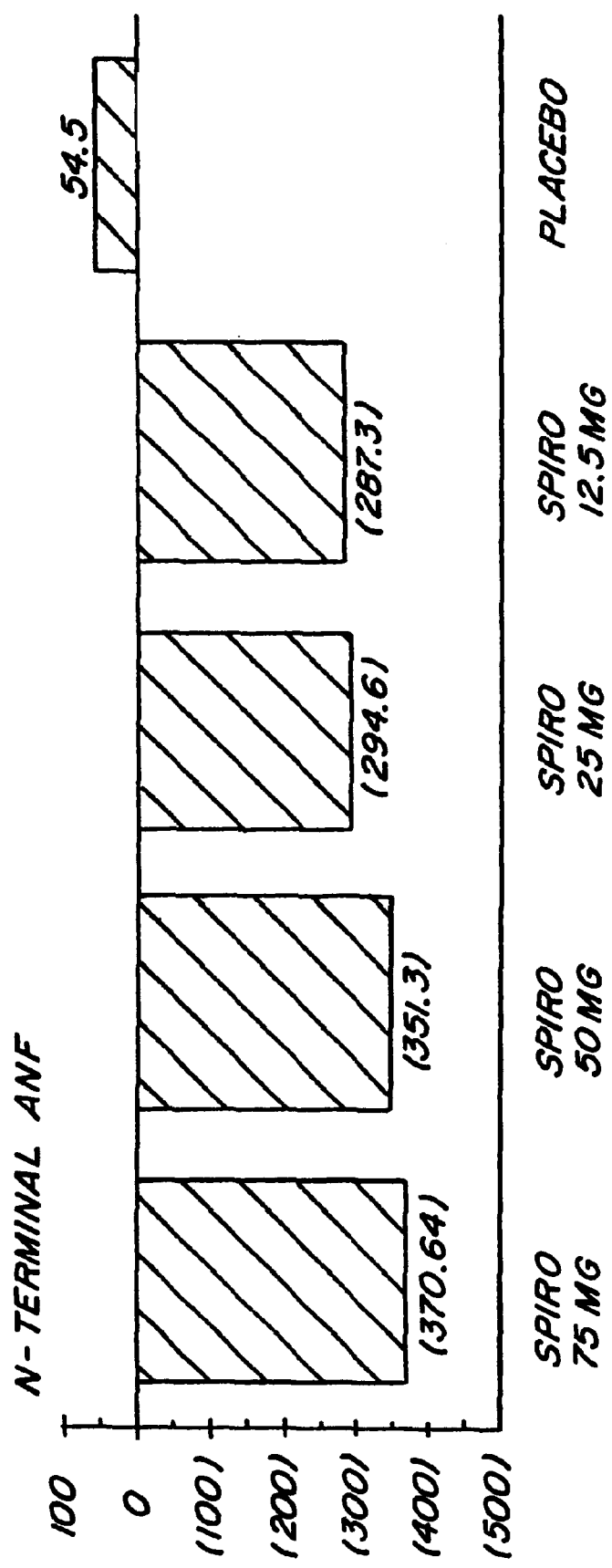
FIG. 3 shows N-Terminal ANF levels at different rates of spironolactone administration (12.5 mg, 25 mg, 50 mg, 75 mg), as compared to placebo, co-administered with stable doses of ACE inhibitor and loop diuretic.
Figure 4:
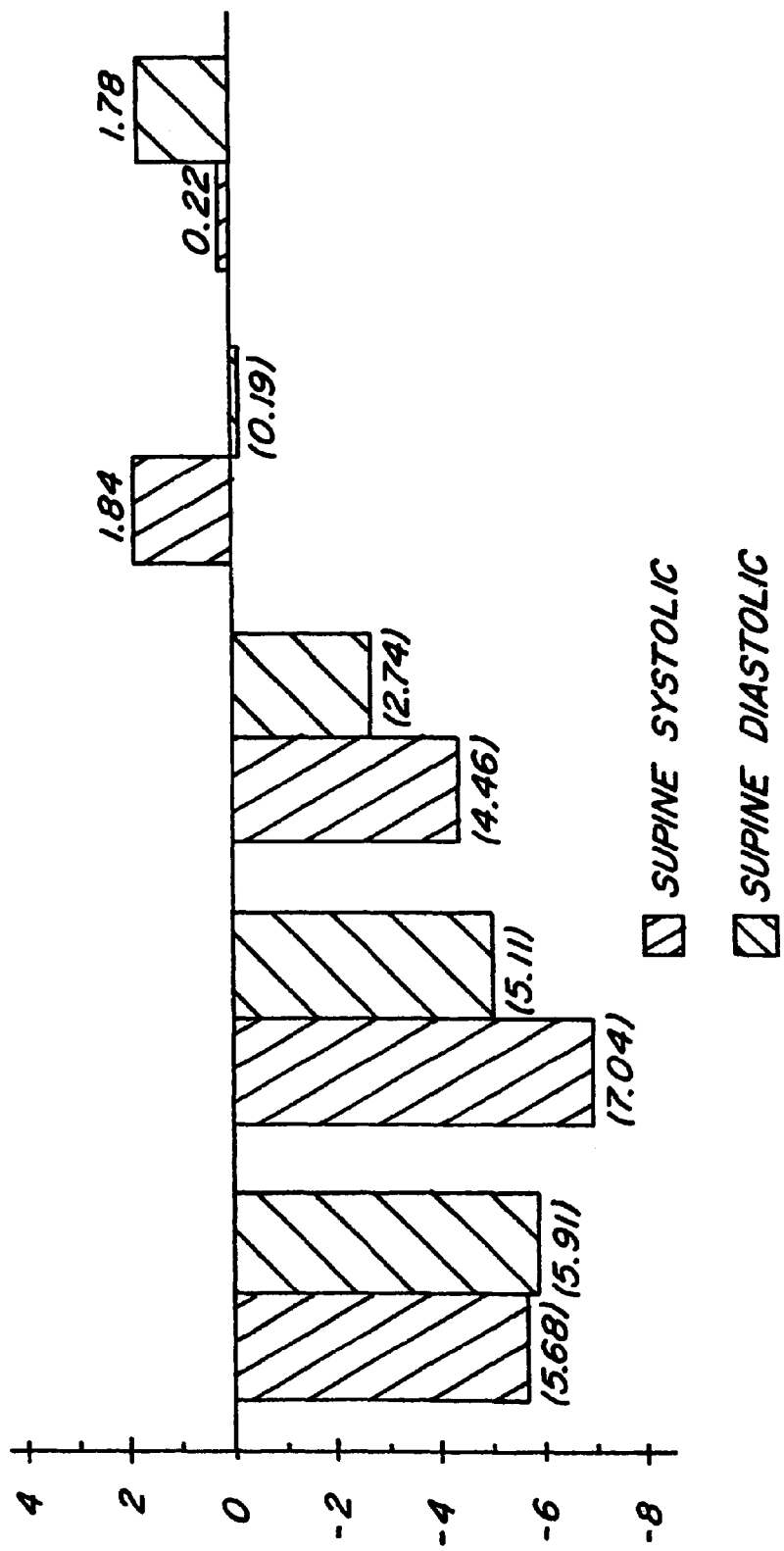
FIG. 4 shows changes in supine blood pressure at different rates of spironolactone administration (12.5 mg, 25 mg, 50 mg, 75 mg), as compared to placebo, co-administered with stable doses of ACE inhibitor and loop diuretic.
Figure 5:
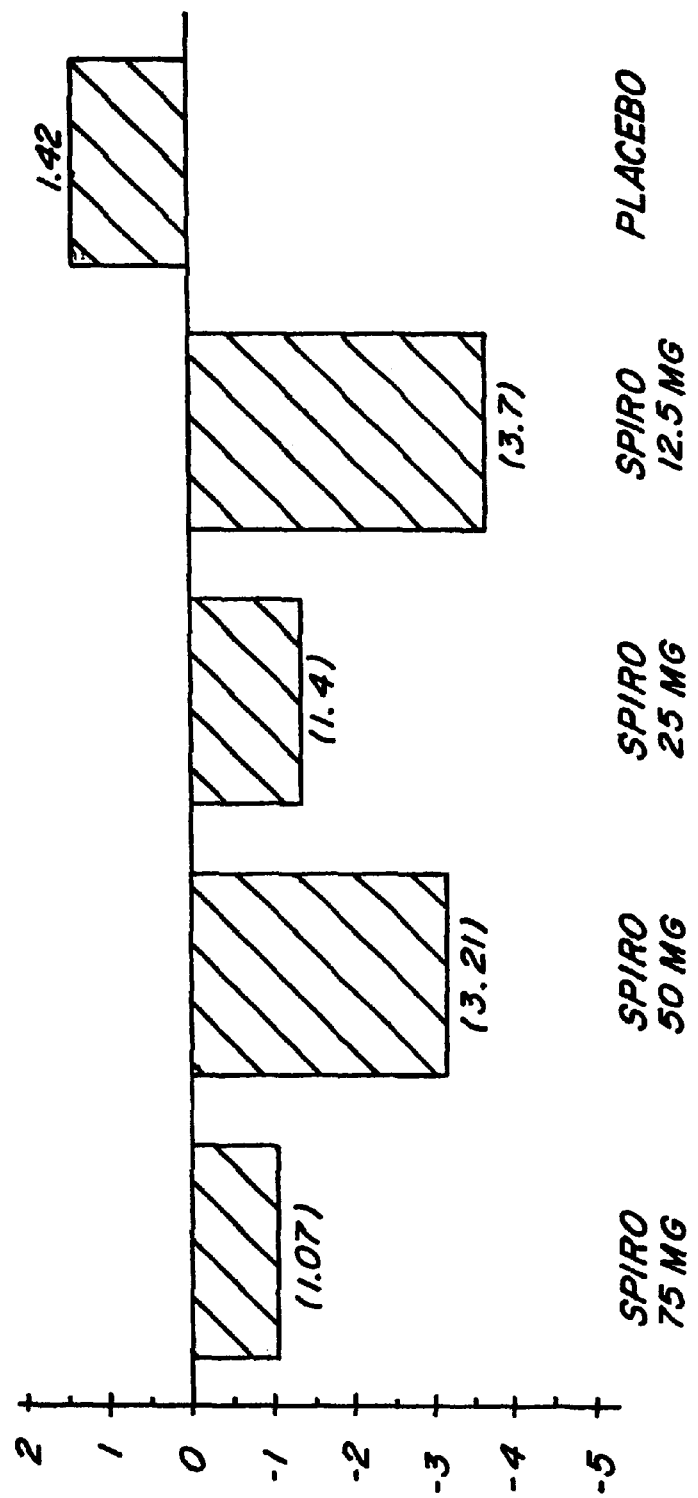
FIG. 5 shows changes in supine heart rate at different rates of spironolactone administration (12.5 mg, 25 mg, 50 mg, 75 mg), as compared to placebo, co-administered with stable doses of ACE inhibitor and loop diuretic.

N-Terminal Atrial Natriuretic Factor (ANF) (See FIG. 3): All active treatments showed decreases from baseline at all treatment visits. Dose-response was statistically significant at Day 9 (p=0.048), Week 4 (p=0.005), and Week 12 (p=0.008). ANF was not measured at Week 8. In comparisons the 50 mg dose group differed significantly from placebo at Week 4 (p=0.009) and Week 12 (p=0.006), while the 75 mg dose group differed significantly from placebo at Week 12 only (p=0.007).

Hematocrit and Hemoalobin: At Day 9 visit a statistically significant mean value difference between placebo and the different active treatments was observed with lower values for the placebo group than the active treatments (p<0.001). At Week 12 a reverse statistically significant difference was observed with lower levels for the active treatment groups for hematocrit (p=0.002) and hemoglobin (0.005).

Serum Potassium: A statistically significant dose-response with respect to change from baseline in serum potassium was seen at all treatment period visits (p<0.001). Higher doses of spironolactone were associated with larger increases in potassium. All doses of active treatment had significantly higher serum potassium levels relative to baseline than placebo ($p \leq 0.034$).

Incidence of Hyperkalemia

| | Treatment: Placebo | Spironolactone 12.5 mg/d | Spironolactone 25 mg/d | Spironolactone 50 mg/d | Spironolactone 75 mg/d |
|---|---|---|---|---|---|
| Patients (%) | 2(5%) | 2(5%) | 6(13%) | 9(20%) | 10(24%) |

Predictors of Hyperkalemia: Seven possible predictors of hyperkalemia (potassium $\geq 5.5$ mmol/L) were included in a step-wise Cox regression analysis: randomized treatment (treated as a categorical variable), age, baseline NYHA class, baseline serum potassium, baseline PRA, baseline creatinine, baseline urinary aldosterone, and type and dose of ACE-I. Besides the dose of spironolactone, the following predictors of hyperkalemia were statistically significant in the step-wise regression analysis: type of ACE-I (captopril versus other), baseline serum creatinine, and baseline serum potassium. Results are summarized as follows:

| Factor | p-value | Risk Ratio |
|---|---|---|
| Captopril vs other ACE-I | 0.013 | 0.318 |
| Serum Creatinine > normal | 0.038 | 2.72 |
| Baseline Potassium > median | 0.040 | 2.32 |

In this analysis, the risk ratio can be thought of as the probability that the patient with the risk factor will develop hyperkalemia, relative to the probability that a patient without the risk factor will develop it. (For example, patients on captopril are about one-third as likely to develop hyperkalemia as a patient on another ACE-I.)

Risk ratios relative to placebo for the various doses of spironolactone are:

| Dose | p-value | Risk Ratio |
|---|---|---|
| Spironolactone 12.5 mg | 0.98 | 1.02 |
| Spironolactone 25 mg | 0.19 | 2.91 |
| Spironolactone 50 mg | 0.034 | 5.32 |
| Spironolactone 75 mg | 0.016 | 6.66 |

After adjusting for the above factors, other predictors included in the step-wise regression analysis were not significant (p-values $\geq 0.07$). However, the following additional factor was significantly related to the development of hyperkalemia when considered apart from other predictors except the dose of spironolactone.

| Factor | p-value | Risk Ratio |
|---|---|---|
| High ACE-I Dose | 0.050 | 2.93 |

Serum Magnesium: Change from baseline in serum magnesium showed a statistically significant dose-response at Day 9 and Week 4 ($p \leq 0.048$), with more patients in the placebo group showing decreases in serum magnesium. However, this effect was not seen at later visits ($p \geq 0.083$).

Adverse Effects: Table V summarizes the twelve most common adverse events by different treatment groups. Only one symptom, hyperkalemia, showed a clear dose-response in term of incidence (p=0.001).

TABLE V

Incidence of Adverse Events
Spironolactone Dose-Ranging Study
Intent-to-Treat Cohort
(Top Twelve Events)

| | Treatment Group (Percentage of Patients) | | | | | |
|---|---|---|---|---|---|---|
| Adverse Events | Spironolactone 12.5 mg | Spironolactone 25 mg | Spironolactone 50 mg | Spironolactone 75 mg | Placebo | Total |
| Dyspnea | 22.0 | 15.6 | 26.1 | 24.4 | 30.0 | 23.5 |
| Angina Pectoris | 19.5 | 20.0 | 8.7 | 14.6 | 17.5 | 16.0 |
| Dizziness | 12.2 | 13.3 | 13.0 | 17.1 | 15.0 | 14.1 |
| Fatigue | 12.2 | 13.3 | 15.2 | 14.6 | 15.0 | 14.1 |
| Nausea | 2.4 | 17.8 | 6.5 | 19.5 | 12.5 | 11.7 |
| Diarrhea | 4.9 | 22.2 | 8.7 | 14.6 | 5.0 | 11.3 |
| Abdominal Pain | 7.3 | 8.9 | 13.0 | 7.3 | 17.5 | 10.8 |
| Headache | 9.8 | 2.2 | 15.2 | 7.3 | 20.0 | 10.8 |
| Hyperkalemia | 2.4 | 8.9 | 15.2 | 19.5 | 2.5 | 9.9 |
| URT Infection | 4.9 | 11.1 | 8.7 | 2.4 | 12.5 | 8.0 |
| Arthralgia | 4.9 | 4.4 | 8.7 | 4.9 | 7.5 | 6.1 |
| Coughing | 4.9 | 2.2 | 4.3 | 2.4 | 12.5 | 5.2 |

A breakdown of the hospitalizations is as follows:

Treatment Placebo 12.5 mg 25 mg 50 mg 75 mg P Patients (%) 5(12.5%) 3(7.3%) 3(6.6%) 13(27.6%) 6(14.6%) N.S. No deaths were reported during the drug treatment period. Three patients died within 30 days after the study was completed. These three patients were previously at the 50 mg dose.

Administration of spironolactone may be accomplished by oral route, or by intravenous, intramuscular or subcutaneous injections. If a diuretic is used in co-therapy, with spironolactone, then administration may take place sequentially in separate formulations, or may be accomplished by simultaneous administration in a single formulation or separate formulations. The formulation may be in the form of a bolus, or in the form of aqueous or non-aqueous isotonic sterile injection solutions or suspensions. These solution and suspensions may be prepared from sterile powders or granules having one or more pharmaceutically-acceptable carriers or diluents, or a binder such as gelatin or hydroxypropylmethyl cellulose, together with one or more of a lubricant, preservative, surface-active or dispersing agent.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. A suitable daily dose for a mammal may vary widely depending on the condition of the patient and other factors. Spironolactone may be present in an amount of from about 1 to 400 mg, preferably from about 2 to 150 mg, depending upon the specific ALDO antagonist compound selected and the specific disease state being targetted for the combination therapy. If a diuretic agent is used in co-therapy, then such agent may be present in an amount from about 1 mg to about 400 mg per dose, and more preferably from about 1 mg to about 150 mg per dose, depending on the diuretic selected.

For disease states which require prevention, reduction or treatment of a cardiovascular disease state without incidence of hyperkalemia, for example, spironolactone will be present in the therapy in an amount in a range from about 1 mg to about 25 mg per dose. A preferred range for spironolactone would be from about 5 mg to 15 mg per dose. More preferably would be a range from about 10 mg to 15 mg per dose per day.

Examples of various ALDO antagonist daily doses of the invention are as follow:

Spironolactone (mg)

5
7.5
10
12.5
15
17.5
20
22.5

The active ingredients may also be administered by injection as a composition wherein, for example, saline, dextrose or water may be used as a suitable carrier.

The dosage regimen for treating a disease condition with the combination therapy of this invention is selected in accordance with a variety of factors, including the type, age, weight, sex and medical condition of the patient, the severity of the disease, the route of administration, and the particular compound employed, and thus may vary widely.

For therapeutic purposes, the active components of this combination therapy invention are ordinarily combined with one or more adjuvants appropriate to the indicated route of administration. If administered per os, the components may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The components may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Pharmaceutical compositions for use in the treatment methods of the invention may be administered in oral form or by intravenous adminstration. Oral administration of the therapy is preferred. Dosing for oral administration may be with a regimen calling for single daily dose, or for a single dose every other day, or for multiple, spaced doses throughout the day. Where a combination therapy is desired, for example, an aldosterone antagonist and a diuretic, the active agents which make up the combination therapy may be administered simultaneously, either in a combined dosage form or in separate dosage forms intended for substantially simultaneous oral administration. The active agents which make up the combinatin therapy may also be administered sequentially, with either active component being administered by a regimen calling for two-step ingestion. Thus, a regimen may call for sequential administration of the active agents with spaced-apart ingestion of the separate, active agents. The time period between the multiple ingestion steps may range from a few minutes to several hours, depending upon the properties of each active agent such a potency, solubility, bioavailability, plasma half-life and kinetic profile of the agent, as well as depending upon the age and condition of the patient. The active agents of the combined therapy whether administered simultaneously, substantially simultaneously, or sequentially, may involve a regimen calling for administration of one active agent by oral route and the other active agent by intravenous route. Whether the active agents of the combined therapy are adminstered by oral or intravenous route, separately or together, each such active agent will be contained in a suitable pharmaceutical formulation of pharmaceutically-acceptable excipients, diluents or other formulations components. Examples of suitable pharmaceutically-acceptable formulations containing the active components for oral administration are given below. Even though such formulations list both active agents together in the same recipe, it is appropriate for such recipe to be utilized for a formulation containing one of the active components.

EXAMPLE 1

An oral dosage may be prepared by screening and then mixing together the following list of ingredients in the amounts indicated. The dosage may then be placed in a hard gelatin capsule.

| Ingredients | Amounts |
| --- | --- |
| spironolactone | 12.5 mg |
| magnesium stearate | 10 mg |
| lactose | 100 mg |

EXAMPLE 2

An oral dosage may be prepared by mixing together granulating with a 10% gelatin solution. The wet granules are screened, dried, mixed with starch, talc and stearic acid, screened and compressed into a tablet.

| Ingredients | Amounts |
| --- | --- |
| spironolactone | 12.5 mg |
| calcium sulfate dihydrate | 100 mg |
| sucrose | 15 mg |
| starch | 8 mg |
| talc | 4 mg |
| stearic acid | 2 mg |

EXAMPLE 3

An oral dosage may be prepared by screening and then mixing together the following list of ingredients in the amounts indicated. The dosage may then be placed in a hard gelatin capsule.

| Ingredients | Amounts |
| --- | --- |
| spironolactone | 12.5 mg |
| furosemide | 73.9 mg |
| magnesium stearate | 10 mg |
| lactose | 100 mg |

EXAMPLE 4

An oral dosage may be prepared by mixing together granulating with a 10% gelatin solution. The wet granules are screened, dried, mixed with starch, talc and stearic acid, screened and compressed into a tablet.

| Ingredients | Amounts |
| --- | --- |
| spironolactone | 12.5 mg |
| furosemide | 73.9 mg |
| calcium sulfate dihydrate | 100 mg |
| sucrose | 15 mg |
| starch | 8 mg |
| talc | 4 mg |
| stearic acid | 2 mg |

Although this invention has been described with respect to specific embodiments, the details of these embodiments are not to be construed as limitations.

What is claimed is:

1. A method to treat a human patient suffering from hypertension, said method comprising administering to said patient an amount of spironolactone sufficient to substantially decrease circulating levels of N-terminal ANF.

2. The method of claim 1 comprising administering spironolactone in an amount that substantially avoids inducing hyperkalemia.

3. The method of claim 1 comprising administering spironolactone in an amount that substantially avoids inducing diuresis.

4. The method of claim 1 wherein said patient is characterized as having an ejection fraction of ≦35%.

5. The method of claim 1 wherein said patient is characterized as having a NYHA Functional classification of II–IV.

* * * * *